(12) United States Patent
Lewallen

(10) Patent No.: US 6,908,486 B2
(45) Date of Patent: Jun. 21, 2005

(54) MODULAR ACETABULAR ANTI-PROTRUSIO CAGE AND POROUS INGROWTH CUP COMBINATION

(75) Inventor: David G. Lewallen, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 10/349,596

(22) Filed: Jan. 23, 2003

(65) Prior Publication Data

US 2003/0171818 A1 Sep. 11, 2003

Related U.S. Application Data

(60) Provisional application No. 60/351,748, filed on Jan. 25, 2002.

(51) Int. Cl.[7] ................................................. A61F 2/32
(52) U.S. Cl. .................................. 623/22.21; 623/22.22
(58) Field of Search ........................... 623/22.21–22.37, 623/17.14, 19.12, 19.11, 20.22, 21.13, 21.16, 23.4

(56) References Cited

U.S. PATENT DOCUMENTS

| | | | | |
|---|---|---|---|---|
| 3,683,421 A | * | 8/1972 | Martinie | 623/22.13 |
| 3,740,769 A | * | 6/1973 | Haboush | 623/22.36 |
| 3,840,904 A | * | 10/1974 | Tronzo | 623/22.32 |
| 3,855,638 A | | 12/1974 | Pilliar | |
| 3,903,549 A | * | 9/1975 | Deyerle | 623/22.36 |
| 3,918,102 A | * | 11/1975 | Eichler | 623/22.39 |
| 4,206,516 A | | 6/1980 | Pilliar | |
| 4,437,193 A | | 3/1984 | Oh | |
| 4,623,351 A | * | 11/1986 | Church | 623/22.25 |
| 4,623,352 A | | 11/1986 | Oh | |
| 4,883,489 A | * | 11/1989 | Grundei et al. | 623/22.36 |

(Continued)

*Primary Examiner*—Alvin Stewart
(74) *Attorney, Agent, or Firm*—Quarles & Brady LLP (57) ABSTRACT

A modular acetabular anti-protrusio cage and acetabular cup combination includes an acetabular cup having a bone ingrowth-promoting surface and a shaped anti-protrusio cage having one or more fixation flanges. The acetabular cup is attached to acetabular bone, and the anti-protrusio cage is thereafter mounted to the inner surface of the acetabular cup. Alternatively, the anti-protrusio cage can be mounted to the inner surface of the acetabular cup before the acetabular cup is attached to acetabular bone. The flanges of the anti-protrusio cage are joined to the ilium, ischium and/or pubis to secure the acetabular cup and the anti-protrusio cage to the hip bone and to distribute forces away from the medial wall of the acetabulum. After the cup and the cage are mounted in the patient, a bearing insert is secured within the interior of the anti-protrusio cage, and a prosthetic femoral head is positioned in the bearing insert.

22 Claims, 7 Drawing Sheets

U.S. PATENT DOCUMENTS

| | | | | |
|---|---|---|---|---|
| 4,904,265 A | * | 2/1990 | MacCollum et al. | 623/22.28 |
| 4,919,675 A | * | 4/1990 | Dietschi | 623/22.26 |
| 4,959,072 A | * | 9/1990 | Morscher et al. | 623/22.33 |
| 5,108,447 A | * | 4/1992 | Zeiler et al. | 623/22.14 |
| 5,197,989 A | * | 3/1993 | Hinckfuss et al. | 623/22.42 |
| 5,222,984 A | * | 6/1993 | Forte | 623/22.18 |
| 5,314,490 A | * | 5/1994 | Wagner et al. | 623/22.36 |
| 5,425,778 A | * | 6/1995 | Zichner et al. | 623/22.29 |
| 5,458,650 A | * | 10/1995 | Carret et al. | 623/22.25 |
| 5,624,464 A | * | 4/1997 | Wagner et al. | 623/22.27 |
| 5,702,477 A | * | 12/1997 | Capello et al. | 623/22.21 |
| 5,702,478 A | * | 12/1997 | Tornier | 623/22.24 |
| 5,734,959 A | | 3/1998 | Krebs et al. | |
| 5,871,548 A | * | 2/1999 | Sanders et al. | 623/22.36 |
| 5,931,870 A | | 8/1999 | Cuckler et al. | |
| 5,980,574 A | * | 11/1999 | Takei et al. | 623/22.21 |
| 5,989,293 A | * | 11/1999 | Cook et al. | 623/22.29 |
| 6,306,173 B1 | * | 10/2001 | Masini | 623/22.32 |
| 6,340,370 B1 | * | 1/2002 | Willert et al. | 623/22.38 |
| 6,416,553 B1 | * | 7/2002 | White et al. | 623/22.38 |
| 6,440,131 B1 | * | 8/2002 | Haidukewych | 606/60 |
| 6,458,161 B1 | * | 10/2002 | Gibbs et al. | 623/22.32 |
| 6,520,995 B2 | * | 2/2003 | Church | 623/22.24 |
| 6,527,809 B1 | * | 3/2003 | Doursounian et al. | 623/22.28 |
| 6,620,200 B1 | * | 9/2003 | Descamps et al. | 623/22.32 |
| 6,682,567 B1 | * | 1/2004 | Schroeder | 623/22.24 |
| 2003/0135281 A1 | * | 7/2003 | Hanssen | 623/22.35 |
| 2005/0021148 A1 | * | 1/2005 | Gibbs | 623/22.12 |

* cited by examiner

MODULAR ACETABULAR ANTI-PROTRUSIO CAGE AND POROUS INGROWTH CUP COMBINATION

CROSS-REFERENCES TO RELATED APPLICATIONS

This application claims the benefit of U.S. Provisional Patent Application No. 60/351,748 filed Jan. 25, 2002.

STATEMENT REGARDING FEDERALLY SPONSORED RESEARCH

Not Applicable.

BACKGROUND OF THE INVENTION

1. Field of the Invention

This invention relates to a modular acetabular anti-protrusio cage and acetabular cup combination for receiving the bearing insert of a hip joint prosthesis.

2. Description of the Related Art

For many years now, prostheses have been implanted in the human body to repair or reconstruct all or part of an articulating skeletal joint, such as the hip joint. The hip joint includes the femur and the pelvis, each of which has a surface for articulation against an adjacent articulation surface of the other bone. The femur has a head having a convex, generally spherically contoured articulation surface. The pelvis includes an acetabulum having a concave, generally spherically contoured articulation surface. The articulation surfaces of the femur and the pelvis form a ball-and-socket type joint.

One or both of the articulation surfaces of the hip joint may fail to perform properly, requiring the defective natural articulation surface to be replaced with a prosthetic articulation surface. In an artificial hip joint, a femoral head and a femoral stem can be used to replace the natural head, stem, and articulating surface of the femur, and an acetabular cup can be used to replace the natural socket and articulating surface of the acetabulum of the pelvis. The artificial femoral stem and head may be an integral unitary component or separate modular components designed to be assembled together. The prosthetic femoral head articulates directly against the artificial acetabular cup. The acetabular cup component is received and fixed within the acetabulum of a pelvis. The pelvis is prepared to receive the acetabular cup by reaming a concavity in the acetabular bone. The acetabular cup component typically has an outer surface conforming to the concavity reamed in the acetabular bone of the pelvis, and an inner bearing cavity for receiving the head of a prosthetic femoral component. The prosthetic femoral head articulates in the bearing cavity of the acetabular cup.

One known type of acetabular cup includes an acetabular shell made of a bio-compatible metal, such as titanium or a titanium or chrome-cobalt alloy, and a bearing insert made of a-material which allows the prosthetic femoral head to move about, such as a bio-compatible polymer (e.g. ultra-high molecular weight polyethylene). Some acetabular shells are attached to the acetabular bone using polymerizable synthetic cement, and others are attached to the bone using mechanical anchoring means such as screws. The shell also can be affixed by a combination of bone screws and bone cement. Still other acetabular shells can be attached to the acetabular bone using a "press-fit" shell in which the shell is inserted forcibly into the acetabular cavity. After the acetabular shell is implanted, the bearing insert is secured within the acetabular shell and the head of the prosthetic femoral component is positioned in the bearing insert.

In some instances, degenerative bone conditions or prior surgery can damage the acetabulum, and particularly its medial wall, to the extent that the acetabulum does not have the integrity to serve as a mounting platform for the acetabular shell. This condition requires a reinforcement prosthesis which is implanted within the acetabulum before the acetabular cup, and at least a portion of which receives the acetabular cup. Such a reinforcement body, sometimes known as an ant-protrusio cage, includes a main body that is at least partially cup-shaped and includes two or more integral radially extending flanges. The anti-protrusio cage is first stabilized within the acetabulum using bone cement or bone screws. Thereafter, the flanges are joined to the ilium, ischium and/or pubis to further secure the cage and to distribute forces away from the medial wall of the acetabulum. Examples of anti-protrusio cages can be found in U.S. Pat. Nos. 5,931,870, 5,871,548, 4,623,352, and 4,437,193.

While known anti-protrusio cages can be useful, they do have certain disadvantages. For example, known anti-protrusio cages often have a complicated configuration with various means for attaching fixation flanges to the body of the anti-protrusio cage. These complicated configurations typically require the use of special acetabular cups that are designed to mate with the anti-protrusio cage. Also, all existing systems involve placing a cage system in host bone and thereafter placing an acetabular component into the cage. As a result, these existing systems do not provide for optional use of a cage after placement of an acetabular cup. In other words, these existing systems do not provide a cage system designed for insertion into an acetabular cup if and when it is determined that this would be advantageous after the acetabular cup has been implanted by the surgeon.

Thus, there exists a need for an anti-protrusio cage that can be used with standard acetabular cups that are commonly used in hip replacement procedures. In particular, there is a need for an improved combination of an acetabular anti-protrusio cage and an acetabular cup that provides for maximum flexibility and does not require the use of specialized acetabular cups that are specifically designed to mate with an anti-protrusio cage. Furthermore, there is a need for a modular acetabular anti-protrusio cage and acetabular cup combination wherein the acetabular cup can be implanted first so that the stability of the acetabular cup can be determined before the cage is put in for support, if and when cage type reinforcement is still required.

SUMMARY OF THE INVENTION

The foregoing needs are met by a modular acetabular anti-protrusio cage and acetabular cup combination according to the invention including an acetabular cup having a porous bone ingrowth-promoting surface and a shaped anti-protrusio cage having one or more fixation flanges. The acetabular cup is attached to the acetabular bone using a press fit, and/or bone screws, and/or bone cement, and the anti-protrusio cage is thereafter mounted to the inner surface of the acetabular cup using a press fit, and/or bone screws, and/or bone cement. Alternatively, the anti-protrusio cage can be mounted to the inner surface of the acetabular cup before the acetabular cup is attached to the acetabular bone. The flanges of the anti-protrusio cage are joined to the ilium, ischium and/or pubis by way of bone cement and/or bone screws to further secure the acetabular cup and the anti-protrusio cage to the hip bone and to distribute forces away from the medial wall of the acetabulum to allow for optimum bone ingrowth on the outer surface of the acetabular cup. After the acetabular cup and the anti-protrusio cage are mounted in the acetabular bone of a patient, a bearing insert (i.e., a socket) is secured within the interior of the anti-protrusio cage, and the head of a prosthetic femoral component is positioned in the bearing insert.

It is therefore an advantage of the present invention to provide an anti-protrusio cage that can be used as needed with standard acetabular cups that are commonly used in routine hip replacement procedures.

It is another advantage of the present invention to provide an improved combination of an acetabular anti-protrusio cage and an acetabular cup that provides for maximum flexibility and does not require the use of specialized acetabular cups that are specifically designed to mate with an anti-protrusio cage.

It is yet another advantage of the present invention to provide a modular acetabular anti-protrusio cage and acetabular cup combination wherein the acetabular cup can be implanted first so that the stability of the acetabular cup can be determined before the cage is put in for support, when and it if is needed.

BRIEF DESCRIPTION OF THE DRAWINGS

These and other features, aspects, and advantages of the present invention will become better understood upon consideration of the following detailed description, appended claims and drawings where:

It should be understood that the drawings are not necessarily to scale, and details which are not necessary for an understanding of the present invention or which render other details difficult to perceive may have been omitted. Like reference numerals will be used to refer to like or similar parts from Figure to Figure in the following description of the invention.

DETAILED DESCRIPTION OF THE INVENTION

The present invention provides a modular acetabular anti-protrusio cage and acetabular cup combination. The invention can be used in primary surgery, in which a prosthesis is being used to reconstruct a joint for the first time, as well as in revision surgery, in which a previously-implanted prosthesis is being replaced with another prosthesis. Looking at FIG. 1, the trial components of the invention are shown. The trial components include an acetabular cup trial 10, a shaped anti-protrusio cage trial 40, and a bearing insert trial component (socket) 80. The acetabular cup trial 10, the shaped anti-protrusio cage trial 40, and the bearing insert trial component (socket) 80 are positioned in a hip to confirm fit and sizing of the three components assembled to create the acetabular assembly as will be hereinafter described.

Figure 1:
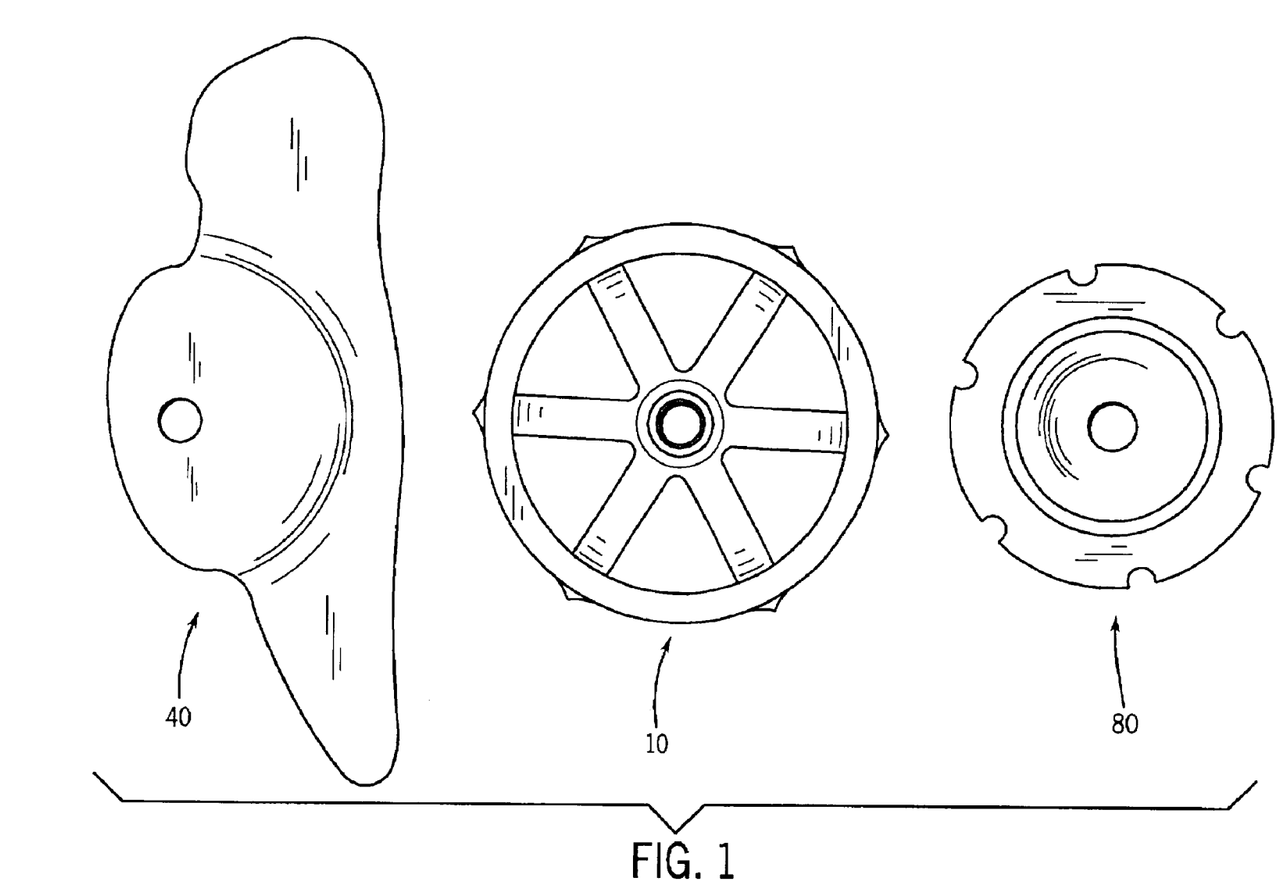
FIG. 1 is a top plan view of an anti-protrusio cage trial, an acetabular cup trial, and a bearing insert trial component (i.e., a socket) that may be used in a modular acetabular anti-protrusio cage and acetabular cup combination according to the present invention.
Figure 2:
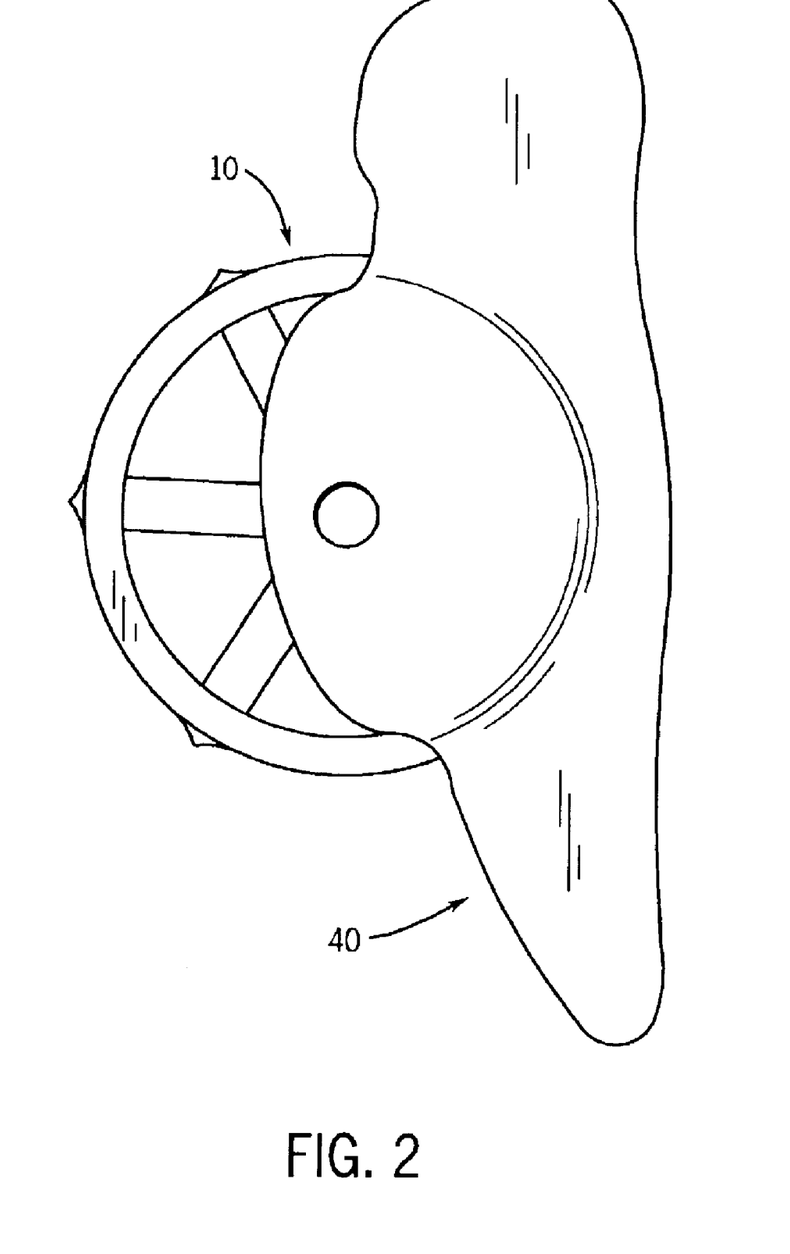
FIG. 2 is a top plan view of the anti-protrusio cage trial of FIG. 1 placed in the acetabular cup trial of FIG. 1.
Figure 3:
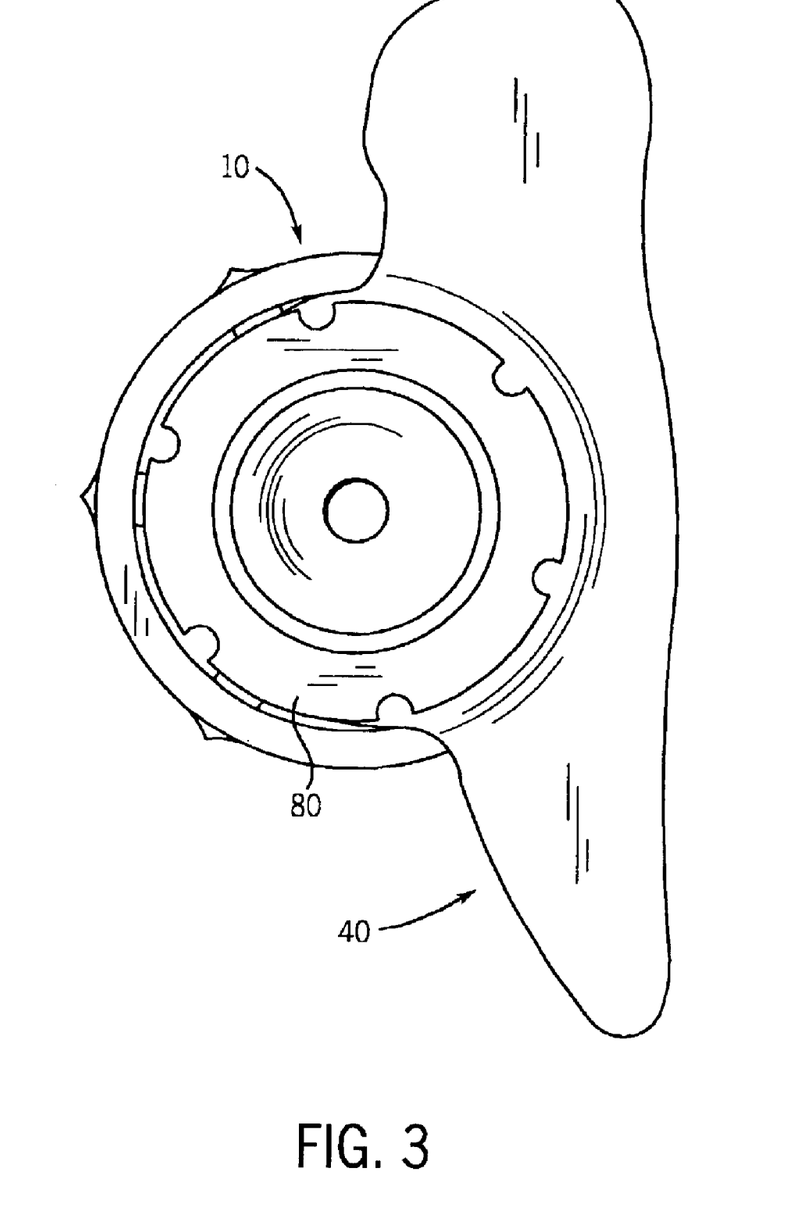
FIG. 3 is a top plan view of the bearing insert trial component (i.e., socket) of FIG. 1 placed in the anti-protrusio cage trial of FIG. 1 which is placed in the acetabular cup trial of FIG. 1. Use of these trial components allows confirmation of fit and sizing of the three components assembled to create the acetabular assembly.

Looking at FIGS. 1–3, the sequence of steps used to assemble a modular acetabular anti-protrusio cage and acetabular cup combination according to the invention and to install the bearing insert within the interior of the anti-protrusio cage is depicted using trial components which would be provided for planning the required reconstruction during surgery. The acetabular cup trial 10 is positioned in the acetabular bone, and the anti-protrusio trial cage 40 is then fit to the inner surface of the acetabular cup trial 10 to confirm proper sizing and fit. The trial bearing insert 80 can then be inserted within the interior of the anti-protrusio trial cage 40 as is generally depicted in FIG. 3 to further confirm proper sizing and fit.

Figure 4:
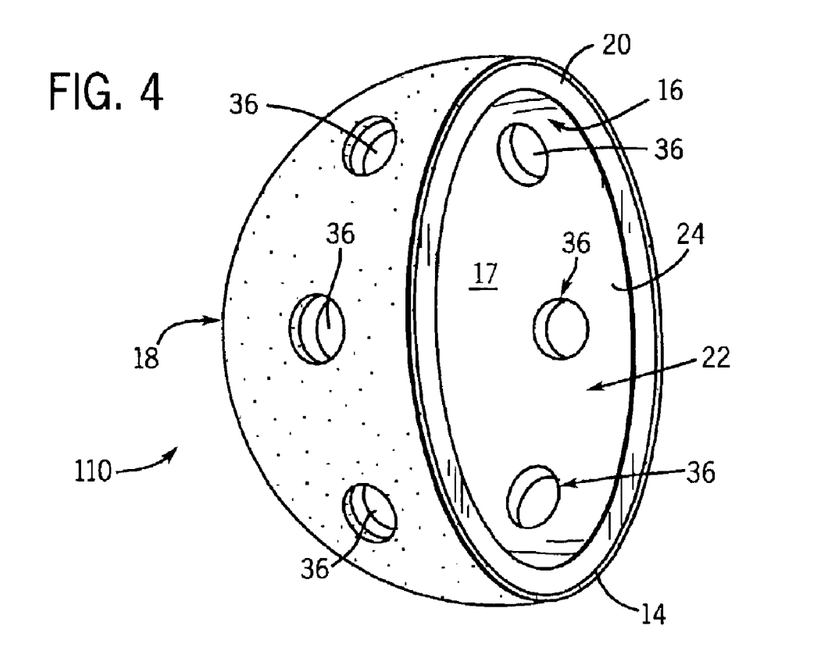
FIG. 4 is a perspective view of real acetabular cup that may be implanted and used in a modular acetabular anti-protrusio cage and acetabular cup combination according to the present invention. Typically, the outer convex surface would have a porous metal surface for bone and tissue ingrowth.
Figure 5:
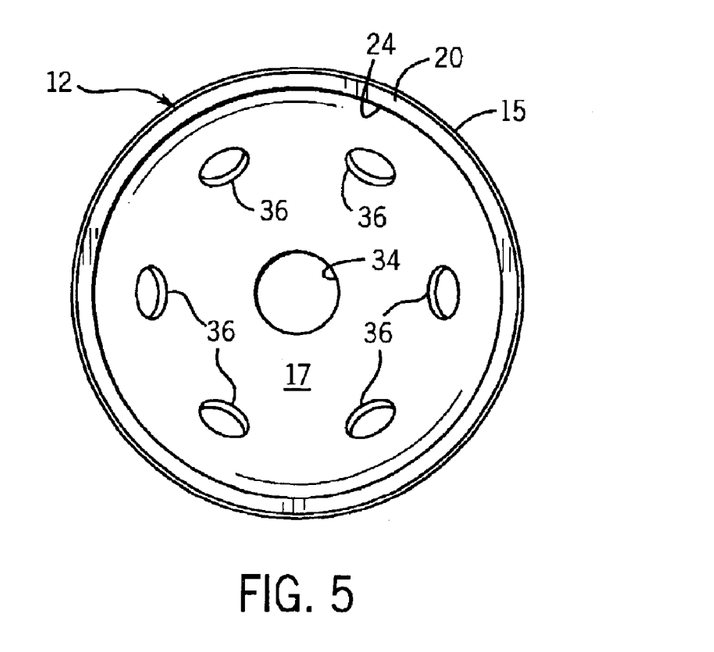
FIG. 5 is a front view of the acetabular cup of FIG. 4.

Having described the trial components of the modular acetabular anti-protrusio cage and acetabular cup combination, example embodiments of the components of the modular acetabular anti-protrusio cage and acetabular cup combination will be described in detail with reference to FIGS. 4–8. Referring first to FIGS. 4 and 5, there is shown an example embodiment of the acetabular cup component of the modular acetabular anti-protrusio cage and acetabular cup combination in accordance with the invention. The illustrated acetabular cup 110 is useful as one component of a well-known hip joint prosthesis that includes an acetabular cup and an associated insert bearing liner, and a femoral stem and an associated spherical head. The spherical head, fixed to the femoral stem, articulates in a ball-and-socket arrangement within the insert bearing liner, with the insert bearing liner being essentially fixed within the acetabular cup. The femoral stem and acetabular cup are fixed to bone of the proximal femur and pelvic acetabulum, respectively.

Figure 8:
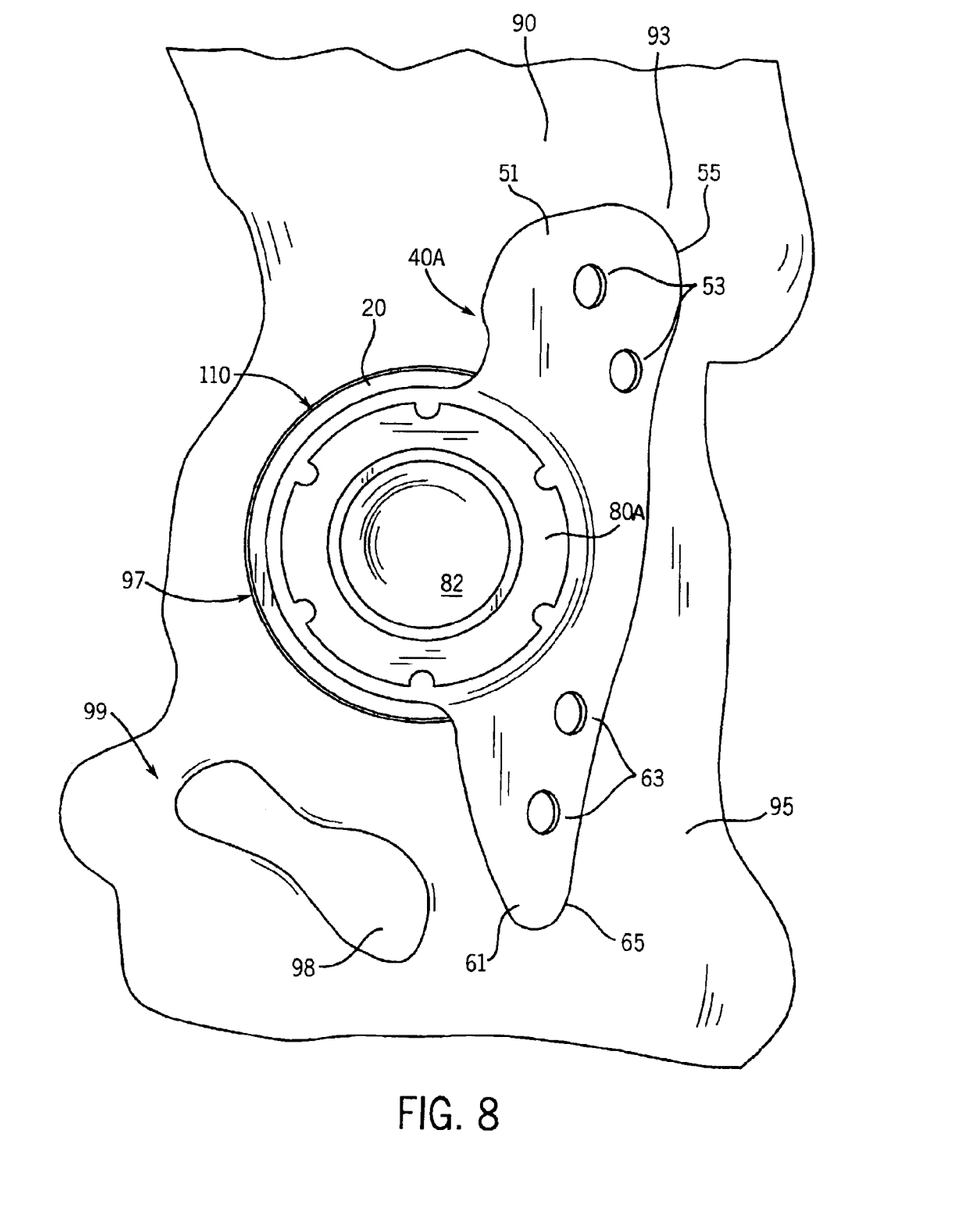
FIG. 8 is a top plan view of a bearing insert (i.e., socket) placed in the anti-protrusio cage of FIG. 6 which is placed in the acetabular cup of FIGS. 4 and 5, which is mounted in a hip. Assembly of the cage into the acetabular cup, and the socket or bearing insert into the cage would preferably be with self-curing acrylic cement (polymethyl methacrylate) but could be by a snap fit or mechanical connection (i.e., locking ring or tabs) between parts.

The acetabular cup 110 is shaped generally as a hemispherical cup having a shell wall 12 comprising an outer wall 14 and an inner wall 16. The acetabular cup 110 has a dome region 18 at the apex of shell wall 12 and an annular rim 20 at the distal end of shell wall 12. The outer wall 14 of shell wall 12 defines an outer surface 15 of the acetabular cup 110. The inner wall 16 of shell wall 12 defines an inner surface 17 which defines a shell cavity 22 having an opening 24 into and through which a bearing insert (socket) 80A as shown in FIG. 8 can be received. The bearing insert 80A is made of a bio-compatible polymer such as ultra high molecular weight polyethylene and has a partially spherical bearing cavity that opens distally for receiving the artificial head of a prosthetic femoral component (not shown) in a conventional ball-and-socket articulating relationship.

The inner wall 16 of the acetabular cup 110 may be formed from a metal alloy such as a titanium alloy (e.g., titanium-6-aluminum-4-vanadium), a cobalt alloy, a stainless steel alloy or of tantalum; a nonresorbable ceramic such as aluminum oxide or zirconia; a nonresorbable polymeric material such as polyethylene; or a nonresorbable composite material such as a carbon fiber-reinforced polymers (e.g., polysulfone). Preferably, the inner wall 16 of the acetabular cup implant is formed from a metal alloy, and most preferably, is formed from titanium or tantalum.

The outer wall 14 of the acetabular cup 110 comprises a porous material, and preferably comprises a porous metallic material having a network of interconnected pores distributed throughout the metallic material chosen to ensure that the resulting interstitial pore size is at least sufficient to permit bone tissue to grow into the porous material for incorporation of the acetabular cup 110 into the acetabular bone. Preferably, the metallic particles are formed from titanium, titanium alloys, cobalt alloys, stainless steel alloys, tantalum, and mixtures thereof. Various methods are known for forming the outer wall 14 of porous material on the inner wall 16, such as the methods described in U.S. Pat. Nos. 5,734,959, 4,206,516 and 3,855,638, which are incorporated herein by reference. The outer surface 15 of the outer wall 14 may also include a textured surface comprising a plurality of depressions such as grooves, dimples, or the like. Further, the outer surface 15 of the outer wall 14 may also have a coating of a bone ingrowth promoting material such as hydroxyapatite ($Ca_{10}(PO_4)_6OH_2$), a calcium phosphate (e.g., tricalcium phosphate ($Ca_3(PO_4)_2$)), growth factors, bone morphogenic proteins, and mixtures thereof.

Referring to FIGS. 4 and 5, the acetabular cup 110 may be provided with a plurality of screw holes 36 which extend through the inner wall 16 and the outer wall 14 of the shell wall 12 in various locations. The inner surface of each screw hole 36 may be configured to receive and/or seat a bone screw (not shown) of a predetermined shape. For instance, the bone screw may include a head and a threaded shank wherein the undersurface of the head of the bone screw (i.e., that portion of the head adjacent the shank) has a truncated cone shape. In this example, the inner surface of the screw holes 36 would be shaped with a countersink to allow the undersurface of the bone screw to seat on the inner surface of the upper portion of the screw hole 36. The screw holes 36 extend completely through the acetabular cup 110, that is, from the inner surface 17 of the acetabular cup 110 to the outer surface 15 of the acetabular cup 110. The screw holes 36 are optional features of the acetabular cup 110 and are not required for use of the acetabular cup 110.

Referring to FIGS. 4 and 5, the acetabular cup 110 may also include a dome hole 34 centered at the apex of dome region 18. The dome hole 34 is configured to serve as an engagement interface for an instrument (not shown) for holding and positioning acetabular cup 110. Typically, such an instrument is used by the implanting physician to securely grasp the acetabular cup and place it in the reamed acetabulum. Looking at FIGS. 4 and 5, it can be seen that the dome hole 34 extends completely through the acetabular cup 110, that is, from the inner surface 17 of the acetabular cup 110 to the outer surface 15 of the acetabular cup 110. The dome hole 34 is optional feature of the acetabular cup 110 is not required for use of the acetabular cup 110.

Figure 6:
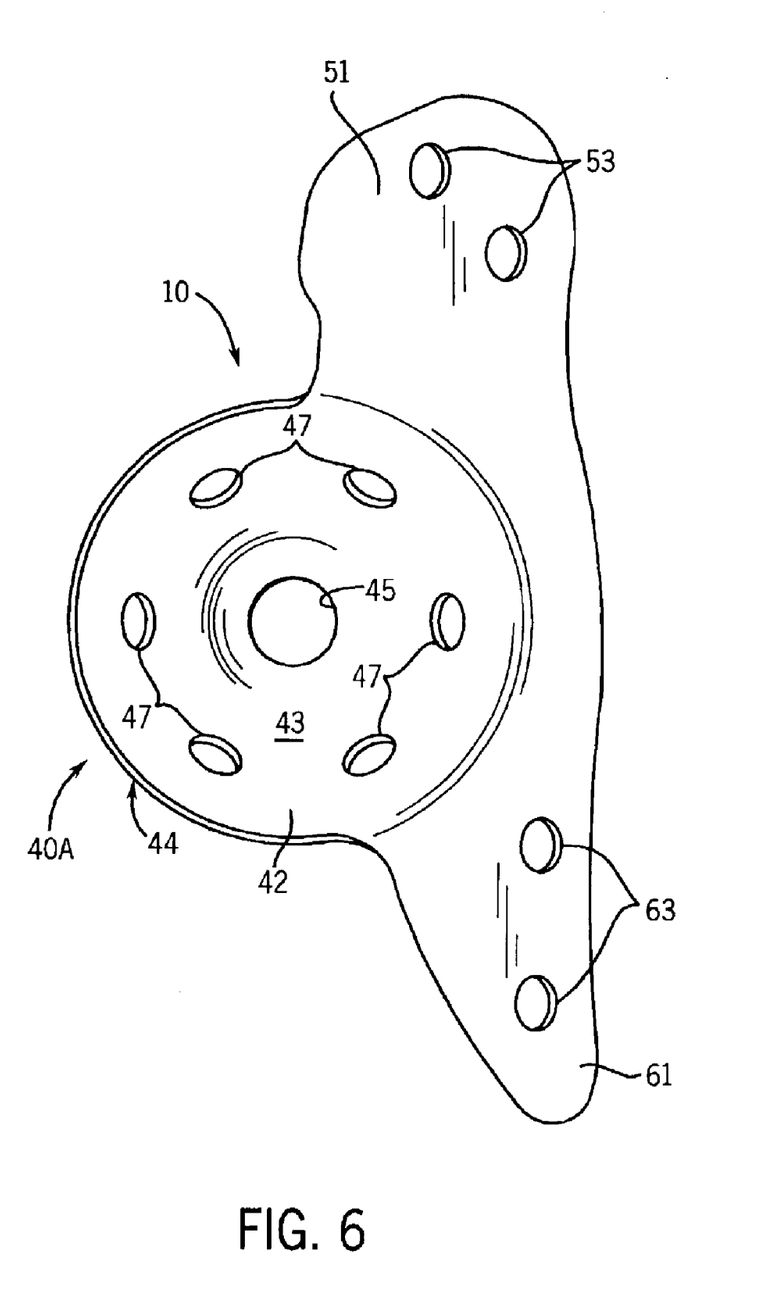
FIG. 6 is a top plan view of an anti-protrusio cage that may be used in a modular acetabular anti-protrusio cage and acetabular cup combination according to the present invention.

Turning now to FIG. 6, there is shown an example embodiment of the anti-protrusio cage component of the modular acetabular anti-protrusio cage and acetabular cup combination in accordance with the invention. The anti-protrusio cage 40A includes a body 42, an ilium fixation flange 51 that extends generally outwardly and upwardly from a right top portion of the body 42, and an ischium fixation flange 61 that extends generally outwardly and downwardly from a right bottom portion of the body 42. The body 42 has a generally hemispherical or partly hemispherical shape. The body 42 includes an inner surface 43 and an outer surface 44 on the opposite side of the body 42. The inner surface 43 of the body 42 is shaped to be suitable for engaging an outer surface of a bearing insert (socket) 80A such as that shown in FIG. 8. The outer surface 44 of the body 42 of the anti-protrusio cage 40A is shaped so as to conform to at least a portion of the inner surface 17 of the acetabular cup 110.

The anti-protrusio cage 40A may be formed (such as by stamping an alloy sheet)from a metal alloy such as a titanium alloy (e.g., titanium-6-aluminum-4-vanadium), a cobalt alloy, a stainless steel alloy or from tantalum; a nonresorbable ceramic such as aluminum oxide or zirconia; a nonresorbable polymeric material such as polyethylene; or a nonresorbable composite material such as a carbon fiber-reinforced polymers (e.g., polysulfone). Preferably, the anti-protrusio cage 40A is formed from a metal alloy, and most preferably, is formed from a titanium alloy or stainless steel alloy.

All sections or certain sections of the surface of the anti-protrusio cage such as the flanges, may be smooth or they may be coated with or be comprised of a porous material, and preferably a porous metallic material having a network of interconnected pores distributed throughout, with e interstitial pore size at least sufficient to permit bone tissue to grow into the porous material for incorporation of sections of the anti-protrusio cage 40A into the supporting bone. Various methods are known for forming the porous material on the surface of implants such as the anti-protrusio cage 40A, such as the methods described in U.S. Pat. Nos. 5,734,959, 4,206,516 and 3,855,638. All sections or certain sections of the surface of the anti-protrusio cage 40A may also include a textured surface comprising a plurality depressions such as grooves, dimples, or the like. Further, all sections or certain sections of the surface of the anti-protrusio cage 40A may also have a coating of a bone ingrowth promoting material such as hydroxyapatite ($Ca_{10}(PO_4)_6OH_2$), a calcium phosphate (e.g., tricalcium phosphate ($Ca_3(PO_4)_2$)), growth factors, bone morphogenic proteins, and mixtures thereof. It is particularly advantageous to provide a porous material, a textured surface, or a coating of a bone ingrowth promoting material on the outer surfaces of the ilium fixation flange 51 and/or the outer surfaces of the ischium fixation flange 61 as described below.

Still referring to FIG. 6, the body 42 of the anti-protrusio cage 40A may be provided with a plurality of screw openings 47 which extend through the body 42 of the anti-protrusio cage 40A in various locations. The inner surface of each screw opening 47 may be configured to receive and/or seat a bone screw (not shown) of a predetermined shape. For instance, the bone screw may include a head and a threaded shank wherein the undersurface of the head of the bone screw (i.e., that portion of the head adjacent the shank) has a truncated cone shape. In this example, the inner surface of the screw openings 47 would be shaped with a countersink to allow the undersurface of the bone screw to seat on the inner surface of the upper portion of the screw opening 47. The screw openings 47 extend completely through the body 42 of the anti-protrusio cage 40A. The screw openings 47 are an optional feature of the body 42 of the anti-protrusio cage 40A and are not necessarily required for use of the anti-protrusio cage 40A. The body 42 of the anti-protrusio cage 40A may also include a dome hole 45 centered at the apex of dome region of the body. The dome hole 45 is configured to serve as an engagement interface for an instrument (not shown) for holding and positioning the anti-protrusio cage 40A during placement into the acetabular cup 110 as will be described below.

Still referring to FIG. 6, the ilium fixation flange 51 that extends outwardly from the body 42 of the anti-protrusio cage 40A may also be provided with a plurality of screw openings 53 which extend through the ilium fixation flange 51 of the anti-protrusio cage 40A in various locations. The inner surface of each screw opening 53 may be configured to receive and/or seat a bone screw (not shown) of a predetermined shape. The screw openings 53 extend completely through the ilium fixation flange 51 of the anti-protrusio cage 40A. The screw openings 53 are an optional feature of the ilium fixation flange 51 of the anti-protrusio cage 40A and are not necessarily required for use of the anti-protrusio cage 40A. Likewise, the ischium fixation flange 61 that extends outwardly from the body 42 of the anti-protrusio cage 40A may also be provided with a plurality of screw openings 63 which extend through the ischium fixation flange 61 of the anti-protrusio cage 40A in various locations. The inner surface of each screw opening 63 may be configured to receive and/or seat a bone screw (not shown) of a predetermined shape. The screw openings 63 extend completely through the ischium fixation flange 61 of the anti-protrusio cage 40A. The screw openings 63 are an optional feature of the ischium fixation flange 61 of the anti-protrusio cage 40A and are not necessarily required for use of the anti-protrusio cage 40A.

Having described the use of trial components to confirm proper fit and sizing and an example acetabular cup 110 and an example anti-protrusio cage 40A that may be used in a modular acetabular anti-protrusio cage and acetabular cup combination according to the invention, various methods for implanting the acetabular cup 110 and the anti-protrusio cage 40A in a pelvis can be described. In a first method for implanting the acetabular cup 110 and the anti-protrusio cage 40A, the acetabular cup 110 is first implanted in a hip as follows. The acetabular cavity of the hip joint is inspected and tools (such as a reamer) may be used to clean material out of the acetabular cavity. Once the acetabular cavity has been prepared, the surgeon can then analyze the remaining bone stock to assess possible points of support and screw fixation of the acetabular cup 110. The surgeon then has a number of options. The surgeon may decide to rely on a "press-fit" (sometimes called an "interference fit") for implantation of the acetabular cup 110 into the end portion of the acetabular cavity of the hip bone. In this case, the acetabular cup 110 is implanted without bone cement or bone screws. The surgeon may also decide to rely on a bone cement (such as polymethylmethacrylate cement) for securing the acetabular cup 110 into the end portion of the acetabular cavity of the hip bone. If the surgeon decides to rely screw fixation, the surgeon can use the screw holes 36 of the acetabular cup 110 as locations for bone screws that are driven into acetabular bone. Any combination of a press fit, and/or bone screws, and/or bone cement may be used to secure the acetabular cup 110 to acetabular bone.

Following the above in accordance with this invention, to manage inadequate bone support, the modular anti-protrusio cage can be added by the treating surgeon for added support of the implant construct. The anti-protrusio cage 40A is press fit and/or screwed and/or cemented (using, for example, polymethylmethacrylate cement) into the cavity 22 of the acetabular cup 110 such that at least a section of the outer surface 44 of the body 42 of the anti-protrusio cage 40A is positioned in abutting relationship with at least a portion of the inner surface 17 of the acetabular cup 110. (As used herein, the term 'abutting relationship' also describes a relationship where bone cement is sandwiched between the two abutting surfaces.) This abutting relationship is possible because at least a section of the outer surface 44 of the body 42 of the anti-protrusio cage 40A has a geometric configuration that substantially conforms to the geometric configuration of the inner surface 17 of the acetabular cup 110. Preferably, the outer surface 44 of the body 42 of the anti-protrusio cage 40A and the inner surface 17 of the acetabular cup 110 have mating convex and concave spherical surfaces, respectively, with a series of progressive sizes of paired cups and cages designed for use together. In this preferred version of the outer surface 44 of the body 42 of the anti-protrusio cage 40A and the inner surface 17 of the acetabular cup 110, the inside diameter of the inner surface 17 of the acetabular cup 110 and the outside diameter of the outer surface 44 of the body 42 of the anti-protrusio cage 40A will be similar. After cementing the body 42 of the anti-protrusio cage 40A in the cavity 22 of the acetabular cup 110, a bearing insert 80A as shown in FIG. 8 is secured within the body 42 of the anti-protrusio cage 40A (using for instance, cement or a mechanical snap or interference fit) and the head of an artificial femoral component is positioned in the bearing insert using known methods.

The first method for implanting the acetabular cup 110 and the anti-protrusio cage 40A in a hip bone provides for the prosthethic support structure shown in FIG. 8. In FIG. 8, there is shown a region of the pelvis 90 having the ilium 93, the ischium 95, the acetabulum 97, the obturator foramen 98 and the pubis 99. The acetabular cup 110 is implanted in the acetabulum 97, the body 42 of the anti-protrusio cage 40A is cemented in the cavity 22 of the acetabular cup 110, and the bearing insert 80A having inner surface 82 is secured within the body 42 of the anti-protrusio cage 40A as described above. In the first method for implanting the acetabular cup 110 and the anti-protrusio cage 40A in a hip, the ilium fixation flange 51 that extends outwardly from the body 42 of the anti-protrusio cage 40A may be secured to the ilium 93 by various means. For instance, the outer surface of the ilium fixation flange 51 may include a porous material, a textured surface, or a coating of a bone ingrowth promoting material that serve to physically or chemically bond the ilium fixation flange 51 to the ilium 93 over various time periods. Alternatively, bone screws (not shown) may be driven into the ilium 93 through the openings 53 in the ilium fixation flange 51. In another alternative, an edge 55 of the ilium fixation flange 51 may be inserted into a slot created in the ilium 93.

Likewise, in the first method for implanting the acetabular cup 110 and the anti-protrusio cage 40A in a hip, the ischium fixation flange 61 that extends outwardly from the body 42 of the anti-protrusio cage 40A may be secured to the ischium 95 by various means. For instance, the outer surface of the ischium fixation flange 61 may include a porous material, a textured surface, or a coating of a bone ingrowth promoting material that serve to physically or chemically bond the ischium fixation flange 61 to the ischium 95 over various time periods. Alternatively, bone screws (not shown) may be driven into the ischium 95 through the openings 63 in the ischium fixation flange 61. In another alternative, an edge 65 of the ischium fixation flange 61 may be inserted into a slot created in the ischium 95.

In a second method for implanting the acetabular cup 110 and the anti-protrusio cage 40A in a hip, the acetabular cup 110 and the anti-protrusio cage 40A are first press fit and/or cemented together (using, for example, polymethylmethacrylate cement) such that at least a section of the outer surface 44 of the body 42 of the anti-protrusio cage 40A is positioned in abutting relationship with at least a portion of the inner surface 17 of the acetabular cup 110. After cementing the body 42 of the anti-protrusio cage 40A in the cavity 22 of the acetabular cup, the acetabular cup 110 is implanted into the acetabulum 97 as in the first method described above (i.e., by way of a press fit and/or bone screws and/or bone cement). After implanting the acetabular cup 110 in the acetabulum 97, the bearing insert 80A is secured within the body 42 of the anti-protrusio cage 40A and the head of a prosthetic femoral component is positioned in the bearing insert 80A as described in the first method above. The second method for implanting the acetabular cup 110 and the anti-protrusio cage 40A in a hip bone also provides for the prosthethic support structure shown in FIG. 8, and can include the techniques for securing the ilium fixation flange 51 to the ilium 93 and the techniques for securing the ischium fixation flange 61 to the ischium 95 as described above with reference to the first method.

Figure 7:
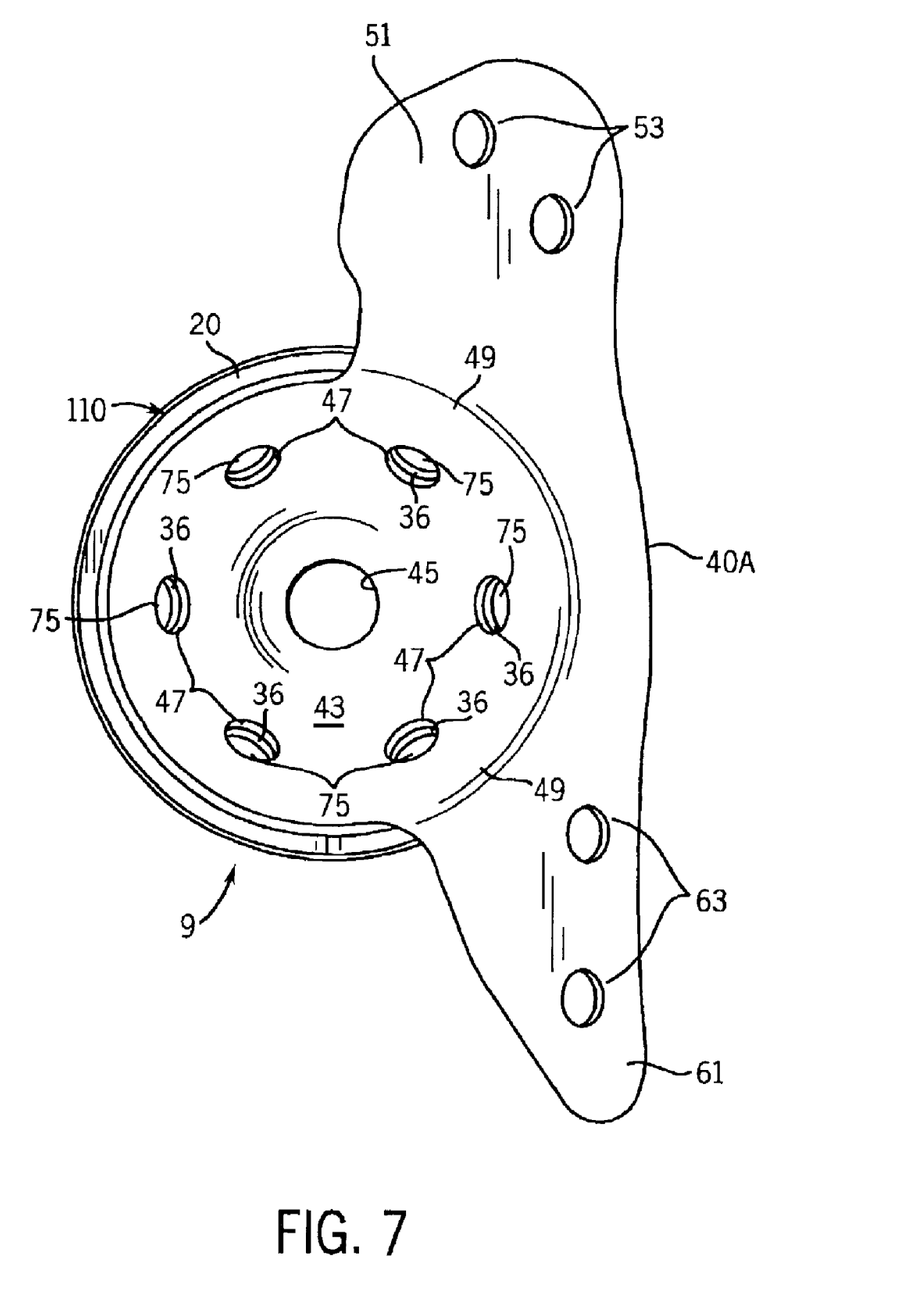
FIG. 7 is a top plan view of the anti-protrusio cage of FIG. 6 placed in the acetabular cup of FIGS. 4 and 5.

In a third method for implanting the acetabular cup 110 and the anti-protrusio cage 40A in a hip, the inner surface 17 of the acetabular cup 110 and the outer surface 44 of the body 42 of the anti-protrusio cage 40A are first positioned in abutting relationship such that the dome hole 34 and screw holes 36 of the acetabular cup 110 line up with the dome hole 45 and the openings 47 of the body 42 of the anti-protrusio cage 40A. This positioning of the acetabular cup 110 and the body 42 of the anti-protrusio cage 40A is shown in FIG. 7. It can be seen from FIG. 7 that the screw holes 36 of the acetabular cup 110 line up with the openings 47 of the body 42 of the anti-protrusio cage 40A to create screw access channels 75 in the modular acetabular anti-protrusio cage and acetabular cup combination indicated generally at 9. The screw holes 36 of the acetabular cup 110 can be maintained in a lined up relationship with the openings 47 of the body 42 of the anti-protrusio cage 40A by press fitting (by way of an interference fit) or cementing the body 42 of the anti-protrusio cage 40A into the acetabular cup 110. In this arrangement of the acetabular cup 110 and the body 42 of the anti-protrusio cage 40A, the ilium fixation flange 51 and the ischium fixation flange 61 extend outwardly from the rim 20 of the acetabular cup 110, and an arcuate ridge 49 (see FIG. 7) of the anti-protrusio cage 40A rides on a portion of the rim 20 of the acetabular cup 110.

After the body 42 of the anti-protrusio cage 40A and the acetabular cup 110 are joined together in the third method and the acetabular bone is prepared as described above, the outer surface 15 of the acetabular cup 110 is placed in contact with the prepared acetabular bone. Optionally, a bone cement may be placed between the outer surface 15 of the acetabular cup 110 and the prepared acetabular bone. Bone screws (not shown) may then be inserted in the screw access channels 75 in the modular acetabular anti-protrusio cage and acetabular cup combination 9 and driven into the acetabular bone. Preferably, the screw access channels 75 include a configuration that snugly seats a bone screw. After implanting the modular acetabular anti-protrusio cage and acetabular cup combination 9, in the acetabulum 97, the bearing insert 80A is secured within the body 42 of the anti-protrusio cage 40A and the head of a prosthetic femoral component is positioned in the bearing insert 80A. The third method for implanting the acetabular cup 110 and the anti-protrusio cage 40A in a hip bone also provides for the prosthethic support structure shown in FIG. 8, and can include the techniques for securing the ilium fixation flange 51 to the ilium 93 and the techniques for securing the ischium fixation flange 61 to the ischium 95 described above.

Various modifications of the anti-protrusio cage 40A are possible. For instance, the anti-protrusio cage (which is shown and described in a left side configuration herein) may include an alternative ilium fixation flange that extends generally outwardly and upwardly from a left top portion of the body, and a pubis fixation flange that extends generally outwardly and downwardly from a left bottom portion of the body. With this alternative configuration of the fixation flanges, the fixation flanges will be secured to ilium and the pubis when the modular acetabular anti-protrusio cage and acetabular cup combination is implanted in the acetabulum. It is also possible to have an ilium fixation flange, an ischium fixation flange and a pubis fixation flange that extend generally outwardly from the body of the anti-protrusio cage. Of course, a right side configuration of the anti-protrusio cage with an ilium fixation flange, and/or an ischium fixation flange, and/or a pubis fixation flange 40A is also contemplated.

The modular acetabular anti-protrusio cage and acetabular cup combination 9 provides for many advantages when used as an acetabular support structure for receiving a socket (and its associated articulating prosthetic femoral head) of a hip joint prosthesis. For instance, by securing the fixation flanges of the acetabular anti-protrusio cage and acetabular cup combination to the ilium and/or the ischium and/or the pubis, any bone ingrowth promoting materials or bone ingrowth promoting configurations (e.g., pores, bone ingrowth promoting material, surface depressions) on the outer surface of the acetabular cup will more quickly provide for a chemical and/or physical bond with the acetabular bone as a portion of the stresses created during loading of the acetabular anti-protrusio cage and acetabular cup combination will be transferred from the acetabular cup to the fixation flanges. When a stronger chemical or physical bond is established between the acetabular cage and the acetabular bone, the bending stresses on the fixation flanges will be lowered thereby minimizing the risks of late fatigue failure of the fixation flanges, a problem often occurring in other known anti-protrusio cages.

The modular nature of the modular acetabular anti-protrusio cage and acetabular cup combination 9 also provides for many advantages. In the situations where an anti-protrusio cage is called for (e.g., where degenerative bone conditions or failed prior surgery or failed implants have seriously deteriorated the acetabulum), a surgeon can mate a standard acetabular cup and the anti-protrusio cage of the present invention to form a highly effective acetabular support structure for receiving a socket of a hip joint prosthesis. There is no need to resort to expensive specialized anti-protrusio cages with associated specialized acetabular cups or expensive specialized anti-protrusio cages having an integral acetabular cup and fixation flanges. Furthermore, the anti-protrusio cage of the present invention provides for numerous means to secure the anti-protrusio cage to existing acetabular cups which are available in a wide range of sizes and numerous means to secure the modular acetabular support structure to various regions of the pelvis. In addition, the modular acetabular anti-protrusio cage and acetabular cup combination allows the acetabular cup to be implanted first so that the stability of the acetabular cup can be determined before the cage is thereafter put in for further support.

While the implantation of a modular acetabular anti-protrusio cage and acetabular cup combination in a pelvis for receiving the bearing insert of a hip joint prosthesis has been illustrated and described herein, one skilled in the art will appreciate that the present invention can be practiced by other than the described embodiments, which have been presented for purposes of illustration and not of limitation. For instance, the methods and prostheses according to the invention can be used as part of the repair of other articulating joints such as the shoulder. Accordingly, the scope of the appended claims should not be limited to the description of the embodiments contained herein.

What is claimed is:

1. A modular acetabular support structure for receiving a socket of a hip joint prosthesis, the structure comprising:

an anti-protrusio cage having a body and at least one fixation flange attached to the body, the body of the anti-protrusio cage having an inner surface suitable for engaging an outer surface of the socket; and an acetabular cup including a wall terminating in a rim defining a cavity of the acetabular cup, the wall having an outer surface and having an inner surface within the cavity of the acetabular cup, at least a portion of the inner surface of the acetabular cup being dimensioned to essentially conform to at least a section of an outer surface of the body of the anti-protrusio cage, wherein at least a part of the anti-protrusio cage is installed in the cavity of the acetabular cup such that the section of the outer surface of the body of the anti-protrusio cage is positioned in abutting relationship with the portion of the inner surface of the acetabular cup and such that each fixation flange extends outwardly from the rim of the wall of the acetabular cup, and wherein the acetabular cup and the anti-protrusio cage are dimensioned such that the socket may be secured within an interior of the anti-protrusio cage after the acetabular cup and the anti-protrusio cage are mounted in acetabular bone of a patient, wherein at least a portion of an edge of the body of the anti-protrusio cage is not attached to the at least one fixation flange.

2. The structure of claim 1 wherein:

the outer surface of the acetabular cup has pores of a size sufficient to permit acetabular bone tissue to grow into the outer surface of the acetabular cup.

3. The structure of claim 1 wherein:

the outer surface of the acetabular cup comprises interconnected metallic particles that define pores of a size sufficient to permit acetabular bone tissue to grow into the outer surface of the acetabular cup.

4. The structure of claim 1 wherein:

the outer surface of the acetabular cup is a textured surface comprising a plurality of depressions.

5. The structure of claim 1 wherein:

the wall of the acetabular cup has a plurality of holes suitable for receiving a bone screw.

6. The structure of claim 1 wherein:

the body of the anti-protrusio cage has a plurality of holes suitable for seating a bone screw.

7. The structure of claim 1 wherein:

the anti-protrusio cage has two fixation flanges arranged in spaced apart relationship such that when the structure is implanted in acetabular bone, one of the fixation flanges can be secured to the ilium and the other of the fixation flanges can be secured to the ischium.

8. The structure of claim 1 wherein:

the body and each fixation flange of the anti-protrusio cage are integral.

9. The structure of claim 1 wherein:

at least one fixation flange of the anti-protrusio cage has an opening suitable for seating a bone screw.

10. The structure of claim 1 wherein:

the wall of the acetabular cup has a plurality of holes, the body of the anti-protrusio cage has a plurality of openings, and the holes of the acetabular cup are positioned in the wall of the acetabular cup and the openings of the anti-protrusio cage are positioned in the body of the anti-protrusio cage such that when the anti-protrusio cage is installed in the cavity of the acetabular cup, the holes and the openings line up to define access channels suitable for seating a bone screw.

11. The structure of claim 1 wherein:

the outer surface of the acetabular cup has a coating of a bone ingrowth promoting material selected from hydroxyapatite, calcium phosphates, growth factors, bone morphogenic proteins, and mixtures thereof.

12. The structure of claim 1 wherein:

a section of an outer surface of each fixation flange has a coating of a bone ingrowth promoting material selected from hydroxyapatite, calcium phosphates, growth factors, bone morphogenic proteins, and mixtures thereof.

13. The structure of claim 1 wherein:

a section of an outer surface of each fixation flange has pores of a size sufficient to permit acetabular bone tissue to grow into the outer surface of each fixation flange.

14. The structure of claim 1 wherein:

a section of an outer surface of each fixation flange comprises interconnected metallic particles that define pores of a size sufficient to permit acetabular bone tissue to grow into the outer surface of each fixation flange.

15. The structure of claim 1 wherein:

a section of an outer surface of each fixation flange is a textured surface comprising a plurality of depressions.

16. The structure of claim 1 wherein:

the section of the outer surface of the body of the anti-protrusio cage is held in abutting relationship with the portion of the inner surface of the acetabular cup by a cement.

17. The structure of claim 1 wherein:

the section of the outer surface of the body of the anti-protrusio cage is held in abutting relationship with the portion of the inner surface of the acetabular cup by screws.

18. The structure of claim 1 wherein:

the section of the outer surface of the body of the anti-protrusio cage is held in abutting relationship with the portion of the inner surface of the acetabular cup by an interference fit.

19. The structure of claim 1 wherein:

an arcuate ridge of the anti-protrusio cage rides on a portion of the rim of the acetabular cup after the cup and the anti-protrusio cage are mounted in a bone of a patient.

20. A modular support structure for receiving a socket of a joint prosthesis, the structure comprising:

an anti-protrusio cage having a body and at least one fixation flange attached to the body, the body of the anti-protrusio cage having an inner surface suitable for engaging an outer surface of the socket; and a cup including a wall terminating in a rim defining a cavity of the cup, the wall having an outer surface and having an inner surface within the cavity of the cup, at least a portion of the inner surface of the cup being dimensioned to essentially conform to at least a section of an outer surface of the body of the anti-protrusio cage, wherein at least a part of the anti-protrusio cage is installed in the cavity of the cup such that the section of the outer surface of the body of the anti-protrusio cage is positioned in abutting relationship with the portion of the inner surface of the cup and such that each fixation flange extends outwardly from the rim of the wall of the cup, and wherein the cup and the anti-protrusio cage are dimensioned such that the socket may be secured within an interior of the anti-protrusio cage after the cup and the anti-protrusio cage are mounted in a bone of a patient, and wherein at least a portion of an edge of the body of the anti-protrusio cage is not attached to the at least one fixation flange.

21. The structure of claim 20 wherein:

the body and each fixation flange of the anti-protrusio cage are integral.

22. The structure of claim 20 wherein:

an arcuate ridge of the anti-protrusio cage rides on a portion of the rim of the acetabular cup after the cup and the anti-protrusio cage are mounted in a bone of a patient.

* * * * *